United States Patent
Tsutaoka

(10) Patent No.: US 11,801,039 B2
(45) Date of Patent: Oct. 31, 2023

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Takuya Tsutaoka, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 450 days.

(21) Appl. No.: 17/223,260

(22) Filed: Apr. 6, 2021

(65) Prior Publication Data

US 2021/0224996 A1    Jul. 22, 2021

Related U.S. Application Data

(63) Continuation of application No. PCT/JP2019/038742, filed on Oct. 1, 2019.

(30) Foreign Application Priority Data

Oct. 12, 2018    (JP) ................. 2018-193269

(51) Int. Cl.
*G06T 5/00* (2006.01)
*G06F 18/2431* (2023.01)
(Continued)

(52) U.S. Cl.
CPC .............. *A61B 8/5223* (2013.01); *A61B 8/08* (2013.01); *A61B 8/5238* (2013.01);
(Continued)

(58) Field of Classification Search
None
See application file for complete search history.

(56) References Cited

U.S. PATENT DOCUMENTS

2013/0184584 A1    7/2013    Berkey
2017/0164924 A1    6/2017    Urabe et al.
(Continued)

FOREIGN PATENT DOCUMENTS

JP    2008-68133 A    3/2008
JP    2012-170749 A    9/2012
(Continued)

OTHER PUBLICATIONS

International Search Report issued in PCT/JP2019/038742; dated Dec. 10, 2019.
(Continued)

*Primary Examiner* — Idowu O Osifade
(74) *Attorney, Agent, or Firm* — Studebaker & Brackett PC

(57) ABSTRACT

An ultrasound diagnostic apparatus 1 includes a bladder pattern storage unit 22, a reference pattern setting unit 21, a bladder extraction unit 18 that extracts a bladder region from an ultrasound image, a bladder extraction success/failure determination unit 19 that determines whether the bladder region represents a bladder having the reference pattern, and an image quality adjustment unit 20 that adjusts the image quality of the ultrasound image in a case where determination is made that the bladder region does not represent the bladder having the reference pattern, in which in a case where the determination is made that the bladder region does not represent the bladder having the reference pattern even in an ultrasound image of which the image quality is adjusted, the bladder extraction success/failure determination unit 19 determines whether the bladder region represents the bladder having the abnormal bladder pattern.

15 Claims, 5 Drawing Sheets

(51) Int. Cl.
  *G06V 10/764* (2022.01)
  *G06V 10/44* (2022.01)
  *A61B 8/08* (2006.01)
  *G06T 7/00* (2017.01)
  *G06V 10/20* (2022.01)
  *A61B 8/00* (2006.01)

(52) U.S. Cl.
  CPC ........ *A61B 8/5269* (2013.01); *G06F 18/2431* (2023.01); *G06T 5/007* (2013.01); *G06T 7/0014* (2013.01); *G06V 10/255* (2022.01); *G06V 10/44* (2022.01); *G06V 10/764* (2022.01); *A61B 8/463* (2013.01); *G06T 2207/10132* (2013.01); *G06T 2207/30084* (2013.01); *G06T 2207/30168* (2013.01); *G06V 2201/031* (2022.01)

(56) References Cited

U.S. PATENT DOCUMENTS

| | | | |
|---|---|---|---|
| 2017/0258386 A1 | 9/2017 | Woltjer et al. | |
| 2017/0296148 A1 | 10/2017 | Niemiec et al. | |
| 2018/0140281 A1 | 5/2018 | Imai | |
| 2018/0357770 A1* | 12/2018 | Choi | G06T 7/13 |
| 2019/0357836 A1* | 11/2019 | Yang | A61B 8/56 |

FOREIGN PATENT DOCUMENTS

| | | |
|---|---|---|
| JP | 2017-109074 A | 6/2017 |
| WO | 2017/017426 A1 | 2/2017 |

OTHER PUBLICATIONS

Written Opinion issued in PCT/JP2019/038742; dated Dec. 10, 2019.

Annangi et al. "An automated bladder volume measurement algorithm by pixel classification using random forests", Conf Proc IEEE Eng Med Biol Soc, Aug. 2016.

Radiology Nation, "Ultrasound Tutorial: Kidney & Bladder / Urinary Tract | Radiology Nation", YouTube video, Jun. 8, 2017, XP055858041, https://youtube.com/watch?v=3X0o1-V1jtE.

Bala K. G. et al., "Ultrasonography of the Urinary Bladder", Journal of Medical Ultrasound, vol. 18, No. 3, Jan. 1, 2010, pp. 105-114, XP027306385, Elsevier, NL.

Cheng Sarah N. et al., "Correlating the Sonographic Finding of Echogenic Debris in the Bladder Lumen With Urinalysis", Journal of Ultrasound in Medicine, vol. 35, No. 7, May 31, 2016, pp. 1533-1540, XP055857721, US.

Breel Robert L. et al., "Pictorial Essay Sonography of Bladder and Perivesical Abnormalities", Jan. 1, 1980, 5 pages total, XP055857753, https://www.ajronline.org/doi/pdf/10.2214/ajr.136.6.1101.

The extended European search report issued by the European Patent Office on Nov. 16, 2021, which corresponds to European Patene No. 19870896.8-1126 and is related to U.S. Appl. No. 17/223,260.

\* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2019/038742 filed on Oct. 1, 2019, which claims priority under 35 U.S.C. § 119(a) to Japanese Patent Application No. 2018-193269 filed on Oct. 12, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus, and more particularly, to an ultrasound diagnostic apparatus and a control method of an ultrasound diagnostic apparatus which are used to measure the urine volume of a subject.

2. Description of the Related Art

Hitherto, in a medical field, an ultrasound diagnostic apparatus using an ultrasound image has been put to practical use. Generally, this kind of ultrasound diagnostic apparatus includes an ultrasound probe having a built-in transducer array and an apparatus body connected to the ultrasound probe, in which ultrasonic waves are transmitted from the ultrasound probe toward a subject, the ultrasound probe receives ultrasound echoes from the subject, and the apparatus body electrically processes the received signal to generate an ultrasound image.

The urine volume of the subject has been measured by examining the bladder of the subject by using such an ultrasound diagnostic apparatus. Upon the examination using the ultrasound diagnostic apparatus, it is preferable that a user who performs the examination has a certain level of skill, but in order for a low-skilled user to easily perform the examination, an ultrasound diagnostic apparatus that, for example, automatically detects and measures a site such as a bladder has been developed. For example, in Annangi P, Fngstad S, Subin S B, Torp A, Ramasubramaniam S, Varna S, "An automated bladder volume measurement algorithm by pixel classification using random forests", Conf Proc IEEE Eng Med Biol Soc, 2016 August, an ultrasound diagnostic apparatus that performs image analysis on the ultrasound image using a machine learning method, thereby automatically detecting a bladder in an ultrasound image and automatically measuring the urine volume based on the detected bladder, is disclosed.

SUMMARY OF THE INVENTION

Incidentally, the bladder of the subject is not always in a normal condition and the bladder of the subject may be in an abnormal condition such as a gas accumulation in the bladder and bladder deformation due to prostatic hypertrophy or the like. As described above, in a case where the bladder is in the abnormal condition, a region representing the bladder may not be correctly extracted and the measurement or the like of the urine volume of the subject may not be correctly performed even by using the ultrasound diagnostic apparatus disclosed in Annangi P, Frigstad S, Subin S B, Torp A, Ramasubramaniam S, Varna S, "An automated bladder volume measurement algorithm by pixel classification using random forests", Conf Proc IEEE Eng Med Biol Soc, 2016 August.

The present invention has been made to solve such a conventional problem and an object thereof is to provide an ultrasound diagnostic apparatus and a control method of an ultrasound diagnostic apparatus capable of improving the accuracy of extracting a bladder.

In order to achieve the above-described object, an ultrasound diagnostic apparatus according to an aspect of the present invention comprises an ultrasound probe; an image acquisition unit that acquires an ultrasound image of a subject by performing transmission and reception of an ultrasound beam to and from the ultrasound probe; a display unit that displays the ultrasound image acquired by the image acquisition unit; a bladder pattern storage unit that stores a normal bladder pattern and an abnormal bladder pattern; a reference pattern setting unit that sets one of the normal bladder pattern and the abnormal bladder pattern stored in the bladder pattern storage unit, as a reference pattern; a bladder extraction unit that extracts a bladder region from the ultrasound image acquired by the image acquisition unit; a bladder extraction success/failure determination unit that determines whether or not the bladder region extracted by the bladder extraction unit represents a bladder having the reference pattern set by the reference pattern setting unit; and an image quality adjustment unit that adjusts an image quality of the ultrasound image, in which in a case where the reference pattern setting unit sets the normal bladder pattern as the reference pattern and the bladder extraction success/failure determination unit determines that the bladder region does not represent a bladder having the reference pattern, the image quality adjustment unit adjusts the image quality of the ultrasound image and the bladder extraction success/failure determination unit determines whether or not the bladder region represents the bladder having the reference pattern for the ultrasound image of which the image quality is adjusted, and in a case where the bladder extraction success/failure determination unit determines that the bladder region does not represent the bladder having the reference pattern even in the ultrasound image of which the image quality is adjusted by the image quality adjustment unit, the reference pattern setting unit sets the abnormal bladder pattern as the reference pattern and the bladder extraction success/failure determination unit determines whether or not the bladder region represents a bladder having the reference pattern consisting of the abnormal bladder pattern.

In a case where the bladder region extracted by the bladder extraction unit has a plurality of concave portions along a circumference of the bladder region and a ratio of a length along the circumference to an area of the bladder region exceeds a predetermined threshold value due to presence of a differential region between a convex hull region of the bladder region and the bladder region, the bladder extraction success/failure determination unit may determine that the bladder region does not represent the bladder having the reference pattern.

Alternatively, in a case where the bladder region extracted by the bladder extraction unit has a concave portion in a central part of a shallow portion and a ratio of an area of a differential region between a convex hull region of the bladder region and the bladder region to an area of the bladder region exceeds a predetermined threshold value, the bladder extraction success/failure determination unit may determine that the bladder region does not represent the bladder having the reference pattern.

In a case where a median value of brightness in the bladder region exceeds a predetermined first threshold value and a variance value of brightness in the differential region is equal to or less than a predetermined second threshold value, the image quality adjustment unit may lower a gain to adjust the image quality of the ultrasound image.

Alternatively, in a case where a difference between a median value of brightness in the bladder region and a median value of brightness in the differential region is equal to or less than a predetermined third threshold value and a variance value of brightness in the differential region exceeds a predetermined fourth threshold value, the image quality adjustment unit may narrow a dynamic range to adjust the image quality of the ultrasound image.

Alternatively, in a case where a brightness gradient from the bladder region to the differential region is equal to or less than a predetermined fifth threshold value, the image quality adjustment unit may narrow a dynamic range to adjust the image quality of the ultrasound image.

In addition, in a case where a ratio of an area of a void portion formed inside the bladder region to an area of the bladder region extracted by the bladder extraction unit exceeds a predetermined threshold value, the bladder extraction success/failure determination unit may determine that the bladder region does not represent the bladder having the reference pattern.

In this case, it is preferable that the image quality adjustment unit lowers a gain to adjust the image quality of the ultrasound image.

In addition, the bladder pattern storage unit may store at least one of a shape of a bladder with an enlarged prostate or cervix, a shape of a bladder with an indwelling balloon, or a shape of a bladder suffering from cystitis, as the abnormal bladder pattern.

In this case, the bladder pattern storage unit may store a plurality of the abnormal bladder patterns, and the reference pattern setting unit may include a pattern classifier that classifies which of the plurality of abnormal bladder patterns stored in the bladder pattern storage unit the bladder region detected by the bladder extraction unit corresponds to.

In addition, the ultrasound diagnostic apparatus may further comprise a guide unit that provides guidance on newly acquiring an ultrasound image by the image acquisition unit, in a case where the bladder extraction success/failure determination unit determines that the bladder region does not represent the bladder having the reference pattern even in a state in which the abnormal bladder pattern is set as the reference pattern by the reference pattern setting unit.

A control method of an ultrasound diagnostic apparatus according to another aspect of the present invention comprises acquiring an ultrasound image of a subject by performing transmission and reception of an ultrasound beam to and from an ultrasound probe; displaying the acquired ultrasound image; storing a normal bladder pattern and an abnormal bladder pattern in a bladder pattern storage unit; setting one of the normal bladder pattern and the abnormal bladder pattern stored in the bladder pattern storage unit, as a reference pattern; extracting a bladder region from the acquired ultrasound image; determining whether or not the extracted bladder region represents a bladder having the set reference pattern; adjusting an image quality of the ultrasound image in a case where determination is made that the bladder region does not represent a bladder having the reference pattern in a state in which the normal bladder pattern is set as the reference pattern; determining whether or not the bladder region represents the bladder having the reference pattern for the ultrasound image of which the image quality is adjusted; and setting the abnormal bladder pattern as a reference pattern in a case where determination is made that the bladder region does not represent the bladder having the reference pattern even in the ultrasound image of which the image quality is adjusted, and determining whether or not the bladder region represents a bladder having the reference pattern consisting of the abnormal bladder pattern.

With the ultrasound diagnostic apparatus according to the aspects of the present invention, in a case where the reference pattern setting unit sets the normal bladder pattern as the reference pattern and the bladder extraction success/failure determination unit determines that the bladder region does not represent the bladder having the reference pattern, the image quality adjustment unit adjusts the image quality of the ultrasound image and the bladder extraction success/failure determination unit determines whether or not the bladder region represents the bladder having the reference pattern for the ultrasound image of which the image quality is adjusted, and in a case where the bladder extraction success/failure determination unit determines that the bladder region does not represent the bladder having the reference pattern even in the ultrasound image of which the image quality is adjusted by the image quality adjustment unit, the reference pattern setting unit sets the abnormal bladder pattern as the reference pattern and the bladder extraction success/failure determination unit determines whether or not the bladder region represents the bladder having the reference pattern consisting of the abnormal bladder pattern. Therefore, the accuracy of extracting the bladder can be improved.

DESCRIPTION OF THE PREFERRED EMBODIMENTS

Hereinafter, an embodiment of the present invention will be described with reference to the accompanying drawings.

Embodiment

Figure 1:
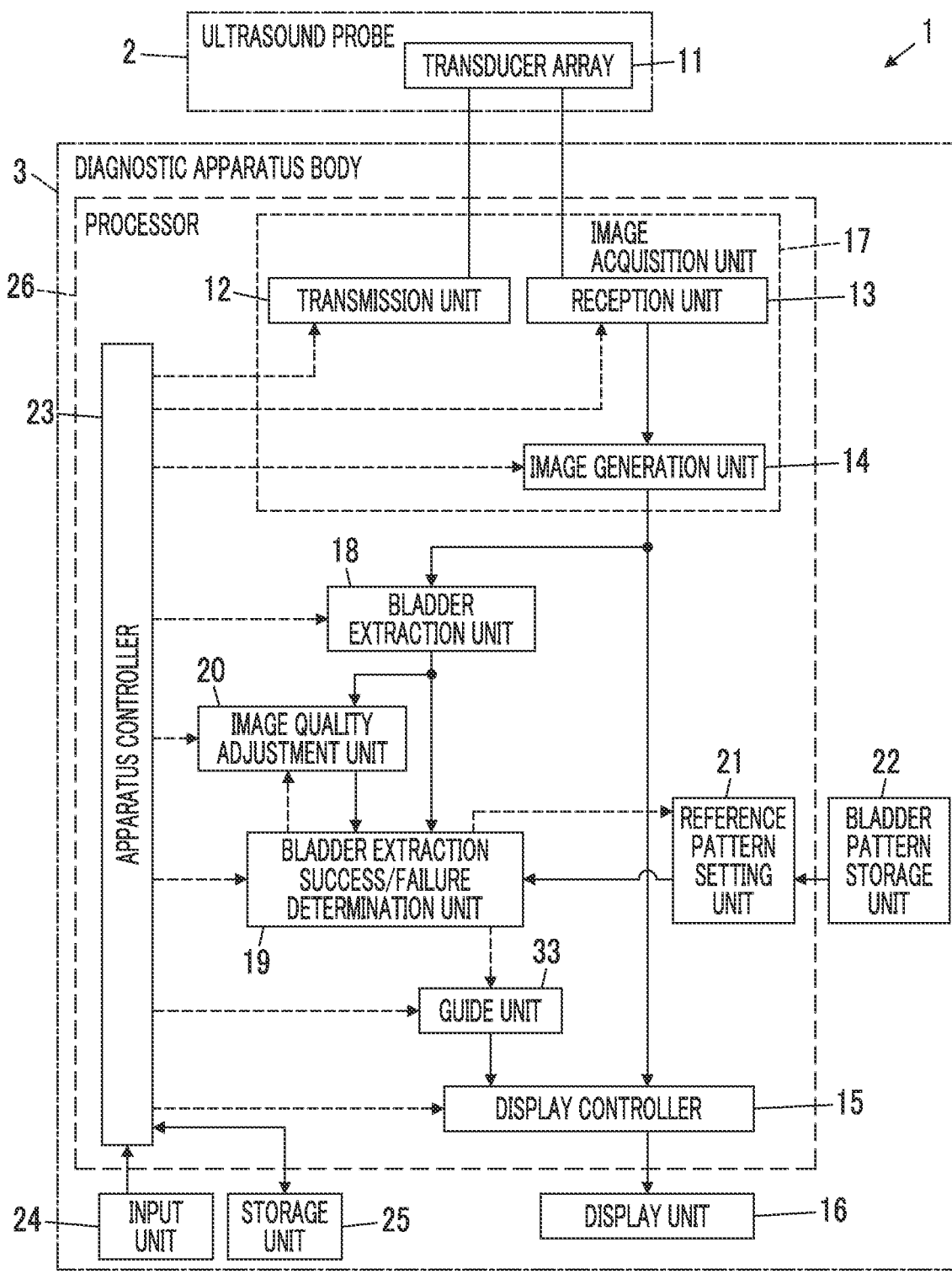
FIG. 1 is a block diagram showing a configuration of an ultrasound diagnostic apparatus according to an embodiment of the present invention.

FIG. 1 shows the configuration of an ultrasound diagnostic apparatus 1. As shown in FIG. 1, the ultrasound diagnostic apparatus 1 has an ultrasound probe 2 and a diagnostic apparatus body 3, and the ultrasound probe 2 and the diagnostic apparatus body 3 are connected to each other. The ultrasound probe 2 comprises a transducer array 11. Here, the ultrasound probe 2 and the diagnostic apparatus body 3 may be connected wiredly or wirelessly to each other.

The diagnostic apparatus body 3 comprises a transmission unit 12 and a reception unit 13, and the transmission unit 12 and the reception unit 13 are connected to the transducer array 11 of the ultrasound probe 2. Further, the reception unit 13 is sequentially connected to the image generation unit 14, the display controller 15, and the display unit 16. Here, the transmission unit 12, the reception unit 13, and the image generation unit 14 constitute an image acquisition unit 17. In addition, a bladder extraction unit 18 is connected to the image generation unit 14, and a bladder extraction success/failure determination unit 19 is connected to the bladder extraction unit 18. An image quality adjustment unit 20 is connected to the bladder extraction unit 18, and the bladder extraction success/failure determination unit 19 is connected to the image quality adjustment unit 20. The reference pattern setting unit 21 is connected to the bladder extraction success/failure determination unit 19, and the bladder pattern storage unit 22 is connected to the reference pattern setting unit 21. A guide unit 33 is connected to the bladder extraction success/failure determination unit 19, and the guide unit 33 is connected to the display controller 15.

Further, the apparatus controller 23 is connected to the transmission unit 12, the reception unit 13, the image generation unit 14, the display controller 15, the bladder extraction unit 18, the bladder extraction success/failure determination unit 19, the image quality adjustment unit 20, and the guide unit 33. The input unit 24 and the storage unit 25 are connected to the apparatus controller 23. Here, the apparatus controller 23 and the storage unit 25 are connected to each other such that information can be exchanged in both directions.

Furthermore, the display controller 15, the image acquisition unit 17, the bladder extraction unit 18, the bladder extraction success/failure determination unit 19, the image quality adjustment unit 20, the reference pattern setting unit 21, the apparatus controller 23, and the guide unit 33 constitute the processor 26.

The transducer array 11 of the ultrasound probe 2 shown in FIG. 1 has a plurality of transducers arranged one-dimensionally or two-dimensionally. Each of the transducers transmits ultrasonic waves in accordance with a drive signal supplied from the transmission unit 12, receives ultrasound echoes from the subject, and outputs the received signal. For example, each transducer is formed by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 12 of the image acquisition unit 17 includes, for example, a plurality of pulse generators, and the transmission unit 12 adjusts the amount of delay of each drive signal based on a transmission delay pattern selected according to a control signal from the apparatus controller 23, and supplies the drive signals to the plurality of transducers so that the ultrasonic waves transmitted from the plurality of transducers of the transducer array 11 form an ultrasound beam. In this manner, in a case where a pulsed or continuous-wave voltage is applied to the electrodes of the plurality of transducers of the transducer array 11, the piezoelectric body expands and contracts to generate pulsed or continuous-wave ultrasonic waves from each transducer. From the combined wave of these ultrasonic waves, the ultrasound beam is formed.

The transmitted ultrasound beam is reflected by a target, for example, a site of the subject, and propagates toward the transducer array 11 of the ultrasound probe 2. The ultrasound echoes propagating toward the transducer array 11 in this manner are received by each transducer constituting the transducer array 11. In this case, each transducer constituting the transducer array 11 expands and contracts by receiving the propagating ultrasound echoes to generate an electrical signal, and outputs the electrical signal to the reception unit 13.

Figure 2:
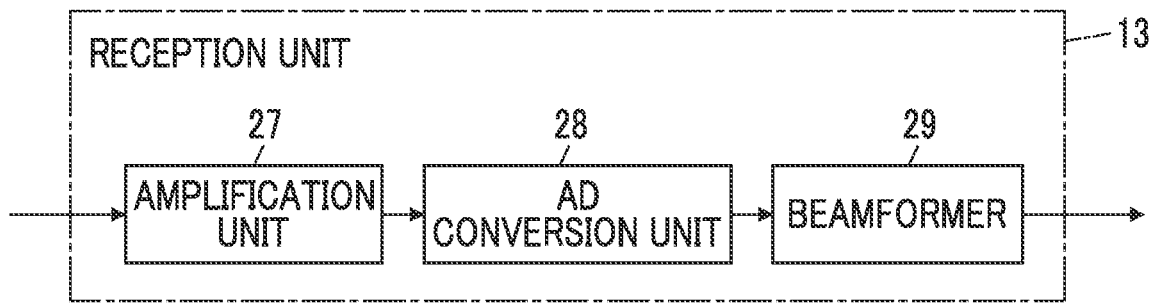
FIG. 2 is a block diagram showing an internal configuration of a reception unit according to the embodiment of the present invention.

The reception unit 13 of the image acquisition unit 17 processes the received signal output from the transducer array 11 based on the control signal from the apparatus controller 23. As shown in FIG. 2, the reception unit 13 has a configuration in which an amplification unit 27, an analog digital (AD) conversion unit 28, and a beamformer 29 are connected to one another in series. The amplification unit 27 amplifies the received signal received from each transducer constituting the transducer array 11, and transmits the amplified received signal to the AD conversion unit 28. The AD conversion unit 28 converts the received signal transmitted from the amplification unit 27 into digital data, and sends the data to the beamformer 29. Based on a reception delay pattern selected according to the control signal from the apparatus controller 23, the beamformer 29 performs reception focusing processing in which addition (phasing addition) is performed by giving delays to respective pieces of data according to a set sound speed. Through the reception focusing processing, a sound ray signal in which the focus of the ultrasound echo is narrowed on a fixed scanning line is generated. The sound ray signal generated in this manner is sent to the image generation unit 14.

Figure 3:
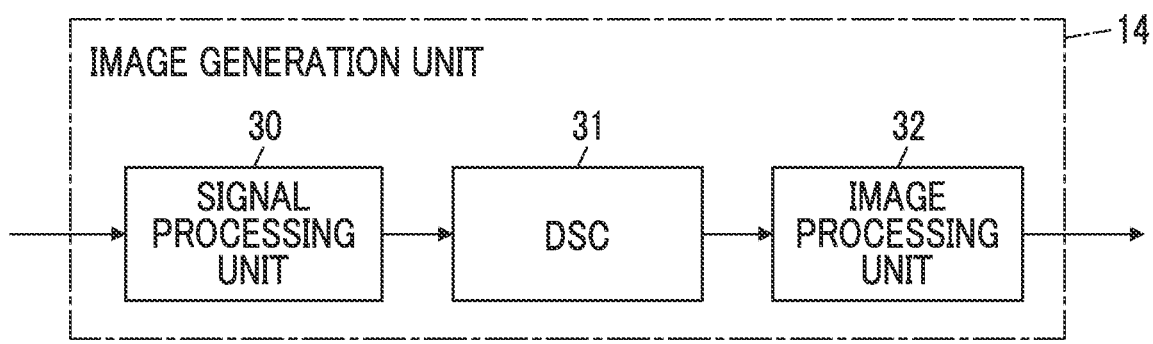
FIG. 3 is a block diagram showing an internal configuration of an image generation unit according to the embodiment of the present invention.

As shown in FIG. 3, the image generation unit 14 of the image acquisition unit 17 has a configuration in which a signal processing unit 30, a digital scan converter (DSC) 31, and an image processing unit 32 are connected to one another in series. The signal processing unit 30 corrects the attenuation of the generated sound ray signal, which is caused by the propagation distance according to the depth of the reflection position of the ultrasonic wave, and then performs envelope detection processing to generate a B-mode image signal representing a tissue in a subject. The B-mode image signal generated in this manner is output to the DSC 31.

The DSC 31 of the image generation unit 14 raster-converts the B-mode image signal into an image signal according to a normal television signal scanning method to generate an ultrasound image. The image processing unit 32 of the image generation unit 14 performs various kinds of necessary image processing such as brightness correction, gradation correction, sharpness correction, and color correction on the image data obtained by the DSC 31, and then outputs the ultrasound image to the display controller 15 and the bladder extraction unit 18.

The bladder extraction unit 18 of the processor 26 performs image analysis on the ultrasound image acquired by the image acquisition unit 17 to extract a region in which a bladder exists, that is, a bladder region. In this case, the bladder extraction unit 18 stores, for example, typical bladder pattern data in advance as a template, calculates the similarity to the pattern data while searching the image with the template, and thereby can extract the place in which the similarity is equal to or more than a threshold value, as the bladder region. In addition to the simple template matching, in order to calculate the similarity, for example, a machine learning method described in Csurka et al.: Visual Categorization with Bags of Keypoints, Proc. of ECCV Workshop on Statistical Learning in Computer Vision. pp. 59 to 74 (2004), a general image recognition method using deep learning described in Krizhevsk et al.: ImageNet Classification with Deep Convolutional Neural Networks, Advances in Neural Information Processing Systems 25, pp. 1106 to 1114 (2012) may be used.

The bladder pattern storage unit 22 of the ultrasound diagnostic apparatus 1 stores data of a normal bladder pattern and data of an abnormal bladder pattern in advance. Here, the normal bladder pattern refers to a typical pattern representing a bladder having a normal shape without any disease or the like. On the other hand, the abnormal bladder pattern refers to a pattern representing a bladder having an abnormal shape different from the normal bladder pattern, due to, for example, a disease such as prostatic hypertrophy or cervical hypertrophy, a so-called indwelling balloon in the bladder, or a subject suffering from cystitis.

As the bladder pattern storage unit 22, for example, recording media such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server may be used.

The reference pattern setting unit 21 of the processor 26 sets one of the normal bladder pattern and the abnormal bladder pattern stored in the bladder pattern storage unit 22 as the reference pattern which is used by the bladder extraction success/failure determination unit 19.

The bladder extraction success/failure determination unit 19 of the processor 26 determines whether or not the bladder region extracted by the bladder extraction unit 18 represents a bladder having the reference pattern set by the reference pattern setting unit 21. In this case, the bladder extraction success/failure determination unit 19 calculates, for example, the similarity between the bladder region extracted by the bladder extraction unit 18 and the reference pattern, and in a case where the similarity is equal to or more than a threshold value, the bladder extraction success/failure determination unit 19 may determine that the bladder region represents the bladder having the reference pattern.

The image quality adjustment unit 20 of the processor 26 adjusts the image quality of the ultrasound image acquired by the image acquisition unit 17 so that the bladder region extracted by the bladder extraction unit 18 is clearly depicted. The image quality adjustment unit 20 analyzes, for example, the intensity of image signal constituting the ultrasound image, that is, brightness of pixels, performs image processing, and thereby adjusts a gain and a dynamic range of the ultrasound image to adjust the image quality of the ultrasound image.

Further, in a case where the reference pattern setting unit 21 sets the normal bladder pattern as the reference pattern, and the bladder extraction success/failure determination unit 19 determines that the bladder region does not include the bladder having the reference pattern consisting of the normal bladder pattern, the image quality adjustment unit 20 adjusts the image quality of the ultrasound image from which the bladder region is extracted by the bladder extraction unit 18.

In a case where the bladder extraction success/failure determination unit 19 determines that the bladder region does not represent the bladder having the reference pattern consisting of the normal bladder pattern even in the ultrasound image of which the image quality is adjusted by the image quality adjustment unit 20, the reference pattern setting unit 21 sets the abnormal bladder pattern as the reference pattern and the bladder extraction success/failure determination unit 19 determines whether or not the bladder region represents the bladder having the reference pattern consisting of the abnormal bladder pattern.

Further, in a case where the bladder extraction success/failure determination unit 19 determines that the bladder region does not have the reference pattern consisting of the abnormal bladder pattern even in a state in which the abnormal bladder pattern is set as the reference pattern by the reference pattern setting unit 21, the guide unit 33 of the processor 26 provides guidance to a user on newly acquiring an ultrasound image by the image acquisition unit 17. In this case, the guide unit 33 may provide guidance to the user by, for example, displaying a text and an image indicating the guidance to the user, on the display unit 16. Further, although not shown, by providing the ultrasound diagnostic apparatus 1 with a voice generation unit, the guide unit 33 may also provide guidance to the user by voice through the voice generation unit.

Under the control of the apparatus controller 23, the display controller 15 of the processor 26 performs predetermined processing on the ultrasound image acquired by the image acquisition unit 17, and causes the display unit 16 to display the ultrasound image.

The display unit 16 of the diagnostic apparatus body 3 displays an image under the control of the display controller 15, and examples thereof include a display device such as a liquid crystal display (LCD) and an organic electroluminescence display (organic EL display).

The apparatus controller 23 of the processor 26 controls each unit of the diagnostic apparatus body 3 based on the program stored in advance in the storage unit 25 or the like and the user's operation through the input unit 24.

The input unit 24 of the diagnostic apparatus body 3 is used for the user to perform an input operation, and may include a keyboard, a mouse, a trackball, a touch pad, a touch panel, and the like.

The storage unit 25 of the diagnostic apparatus body 3 stores an operation program or the like of the diagnostic apparatus body 3, and as the storage unit 25, for example, recording media such as an HDD, an SSD, an FD, an MO disc, an MT, a RAM, a CD, a DVD, an SD card and a USB memory, or a server may be used, as in the bladder pattern storage unit 22.

Here, in the diagnostic apparatus body 3, the processor 26 having the display controller 15, the image acquisition unit 17, the bladder extraction unit 18, the bladder extraction success/failure determination unit 19, the image quality adjustment unit 20, the reference pattern setting unit 21, the apparatus controller 23, and the guide unit 33 may be configured by a central processing unit (CPU) and a control program for causing the CPU to execute various kinds of processing, by using a field programmable gate array (FPGA), a digital signal processor (DSP), an application specific integrated circuit (ASIC), or other integrated circuits (IC), or by combination thereof.

Alternatively, the display controller 15, the image acquisition unit 17, the bladder extraction unit 18, the bladder extraction success/failure determination unit 19, the image quality adjustment unit 20, the reference pattern setting unit 21, the apparatus controller 23, and the guide unit 33 of the processor 26 may be configured by being integrated partially or entirely into one CPU.

Figure 4:
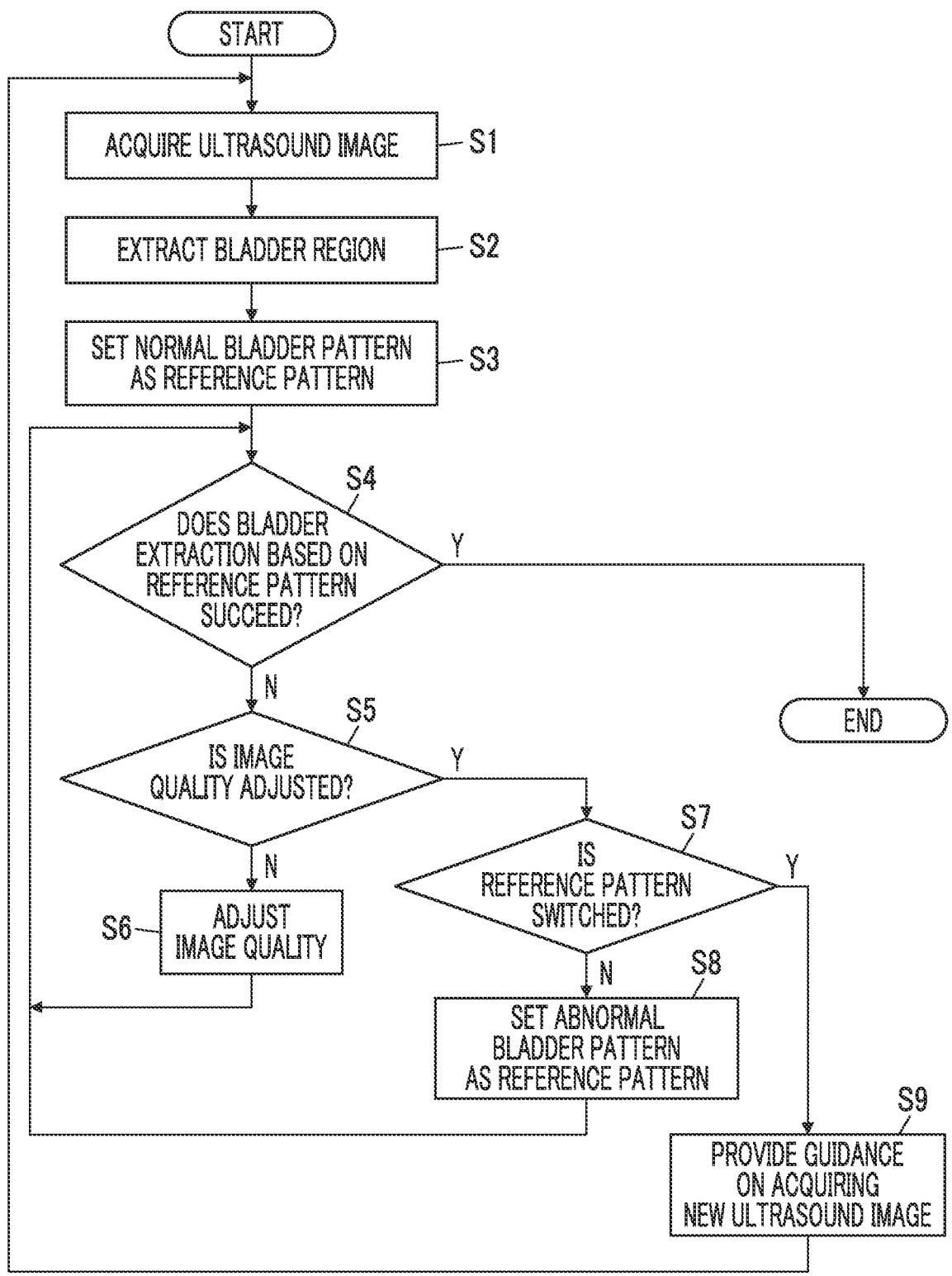
FIG. 4 is a flowchart showing an operation of the ultrasound diagnostic apparatus according to the embodiment of the present invention.

Next, the operation of the ultrasound diagnostic apparatus 1 according to the embodiment of the present invention will be described with reference to the flowchart shown in FIG. 4.

First, in Step S1, in a state in which the ultrasound probe 2 is in contact with the lower abdomen of the subject by the user's operation, the ultrasound beam is transmitted from the transducer array 11 toward the inside of the subject and the ultrasound echo from the subject is received by the transducer array 11. Thereby, in a case where the received signal is output from the transducer array 11 to the image acquisition unit 17, the image acquisition unit 17 generates an ultrasound image representing a tomographic image of the lower abdomen of the subject.

Next, in Step S2, the bladder extraction unit 18 performs image analysis on the ultrasound image acquired in Step S1, and thereby extracts the bladder region in the ultrasound image.

In Step S3, the reference pattern setting unit 21 sets the normal bladder pattern stored in the bladder pattern storage unit 22 as the reference pattern which is used by the bladder extraction success/failure determination unit 19.

Figure 5:
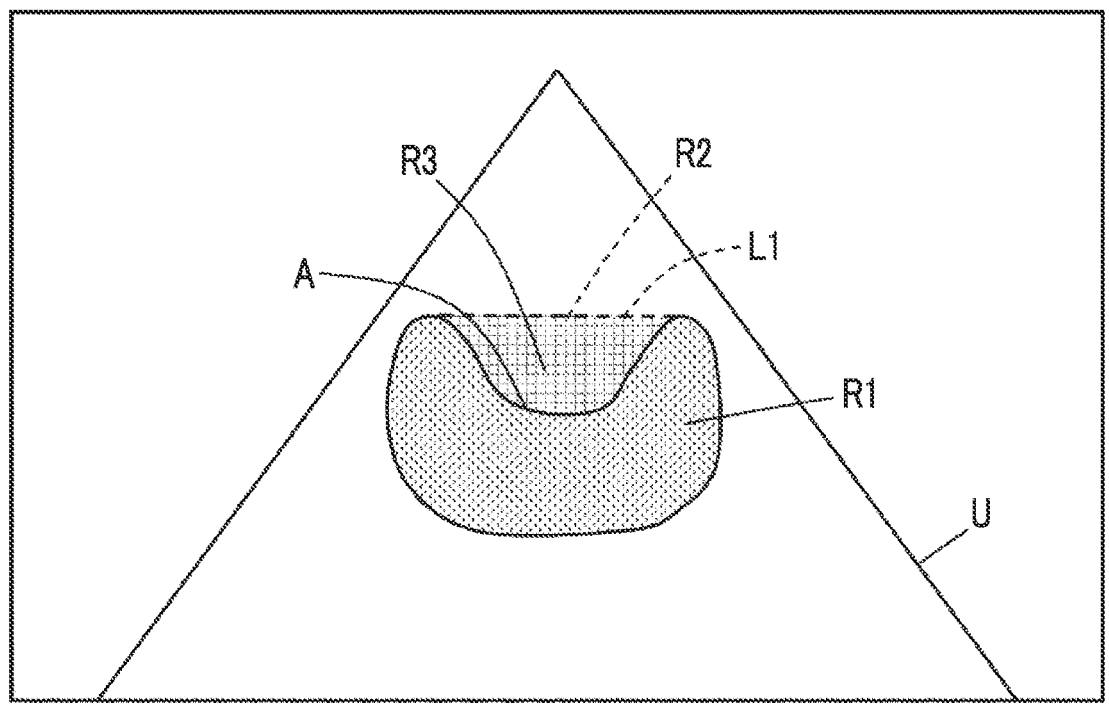
FIG. 5 is a diagram schematically showing an example of a bladder region.

In Step S4, the bladder extraction success/failure determination unit 19 determines whether or not the bladder region extracted in Step S2 represents the reference pattern consisting of the normal bladder pattern set in Step S3. Here, as shown in FIG. 5, for example, in a case where the bladder region R1 in the ultrasound image U has a concave portion A in the central part of the shallow portion, and a ratio of an area of a differential region R3 between a convex hull region R2 of the bladder region R1 and the bladder region R1 to an area of the bladder region R1 exceeds a predetermined threshold value, the bladder extraction success/failure determination unit 19 determines that the bladder region R1 does not represent the reference pattern consisting of the normal bladder pattern, and the process proceeds to Step S5. Here, in a case where a straight line L1 closing the opening of the concave portion A of the bladder region R1 is defined, the convex hull region R2 refers to a region including the bladder region R1, which is surrounded by the straight line L1 and the contour line of the bladder region R1 other than the concave portion A. The differential region R3 is a region obtained by subtracting the bladder region R1 from the convex hull region R2, that is, a region surrounded by the contour line of the concave portion A of the bladder region R1 and the straight line L1.

In Step S5, determination is made whether or not the image quality is already adjusted for the ultrasound image U acquired in Step S1. At this time, the image quality of the ultrasound image U acquired in Step S1 is not adjusted and thus the process proceeds to Step S6.

In Step S6, the image quality adjustment unit 20 analyzes the brightness of the pixels in the ultrasound image U acquired in Step S1 and adjusts the image quality such that the bladder region R1 extracted in Step S2 is clearly depicted. As shown in FIG. 5, for example, in a case where the bladder region R1 has the concave portion A in the central part of the shallow portion, and in a case where a median value of brightness in the bladder region R1 exceeds a predetermined first threshold value and a variance value of brightness in the differential region R3 is equal to or less than a predetermined second threshold value, the image quality adjustment unit 20 determines that the bladder is depicted too brightly due to a high gain in the ultrasound image U. Then, the image quality adjustment unit 20 lowers a gain, and thereby can adjust the image quality of the ultrasound image U. In this manner, the image quality is adjusted such that the bladder region R1 is clearly depicted, so that the accuracy of extracting the bladder can be improved.

When the image quality adjustment in Step S6 is completed, the process returns to Step S4. In Step S4, the bladder extraction success/failure determination unit 19 determines whether or not the bladder region R represents the reference pattern consisting of the normal bladder pattern set in Step S3 for the ultrasound image U of which the image quality is adjusted in Step S6. In Step S4, in a case where determination is made that the bladder region R1 represents the reference pattern, the operation of the ultrasound diagnostic apparatus 1 ends.

On the other hand, in a case where determination is made in Step S4 that the bladder region R1 does not represent the reference pattern consisting of the normal bladder pattern even though the image quality is adjusted in Step S6, the process proceeds to Step S5. Then, determination is made whether the image quality of the ultrasound image U is adjusted. At this time, the image quality is already adjusted in Step S6 and thus the process proceeds to Step S7.

In Step S7, determination is made whether or not the reference pattern consisting of the normal bladder pattern is switched to the reference pattern consisting of the abnormal bladder pattern. At this time, the switching of such a reference pattern is not performed and thus the process proceeds to Step S8.

In Step S8, the reference pattern setting unit 21 sets the abnormal bladder pattern as the reference pattern. Thereby, the bladder region having the abnormal shape can be extracted and thus the bladder in the abnormal condition can be extracted.

When Step S8 is completed, the process returns to Step S4. In Step S4, the bladder extraction success/failure determination unit 19 determines whether or not the bladder region R1 represents the reference pattern consisting of the abnormal bladder pattern set in Step S8 for the ultrasound image U of which the image quality is adjusted in Step S6. In Step S4, in a case where determination is made that the bladder region R represents the reference pattern consisting of the abnormal bladder pattern, the operation of the ultrasound diagnostic apparatus 1 ends.

On the other hand, in a case where determination is made in Step S4 that the bladder region R1 does not represent the reference pattern even though the reference pattern is switched to the reference pattern consisting of the abnormal bladder pattern in Step S8, the process proceeds to Step S5. Then, determination is made whether the image quality of the ultrasound image U is adjusted. At this time, the image quality is already adjusted in Step S6 and thus the process proceeds to Step S7.

In Step S7, determination is made whether or not the reference pattern is already switched from the normal bladder pattern to the abnormal bladder pattern. At this time, the reference pattern is already switched in Step S8 and thus the process proceeds to Step S9.

In Step S9, the guide unit 33 provides guidance to the user on acquiring a new ultrasound image. In this case, the guide unit 33 provides guidance to the user by displaying, for example, a text and an image indicating the guidance on acquiring a new ultrasound image, on the display unit 16. In this way, when Step S9 is completed, the process returns to Step S1 and then a new ultrasound image is acquired. In the subsequent operations, the bladder region R1 is newly extracted by using the acquired new ultrasound image.

As described above, with the ultrasound diagnostic apparatus 1 according to the embodiment of the present invention, first, in a case where the reference pattern setting unit 21 sets the normal bladder pattern as the reference pattern and the bladder extraction success/failure determination unit 19 determines that the bladder region R1 does not represent the reference pattern consisting of the normal bladder pattern, the image quality adjustment unit 20 adjusts the image quality of the ultrasound image U. and in a case where the bladder extraction success/failure determination unit 19 determines that the bladder region R1 does not represent the reference pattern consisting of the normal bladder pattern even in the ultrasound image U of which the image quality is adjusted by the image quality adjustment unit 20, the reference pattern setting unit 21 sets the abnormal bladder pattern as the reference pattern and then the bladder extraction success/failure determination unit 19 determines whether or not the bladder region R1 represents the bladder having the reference pattern consisting of the abnormal bladder pattern. Therefore, the accuracy of extracting the bladder can be improved.

Specific examples of the method for adjusting the image quality by the image quality adjustment unit 20 include lowering a gain of the ultrasound image U based on a median value of brightness of the bladder region R1 and a variance value of brightness in the differential region R3 with reference to FIG. 5, but the method for adjusting the image quality is not limited thereto.

For example, in a case where the difference between a median value of brightness in the bladder region R1 and a median value of brightness in the differential region R3 is equal to or less than a predetermined third threshold value and a variance value of brightness in the differential region R3 exceeds a predetermined fourth threshold value, the image quality adjustment unit 20 determines that a too wide dynamic range in the ultrasound image U causes the generation of noise. Then, the image quality adjustment unit 20 narrows the dynamic range, and thereby can adjust the image quality in the ultrasound image U.

Figure 6:
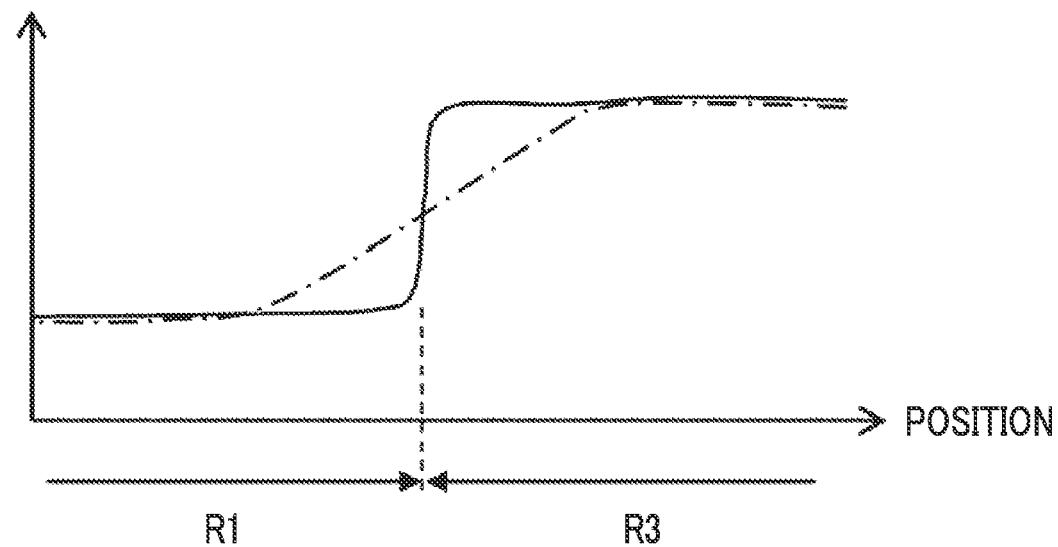
FIG. 6 is a diagram showing a brightness distribution of an ultrasound image from the bladder region to a differential region.

Further, as shown by a dashed line in FIG. 6, for example, in a case where the brightness gradient from the bladder region R1 to the differential region R3 is equal to or less than a predetermined fifth threshold value, the image quality adjustment unit 20 determines that the shape of the bladder is not clearly depicted due to the low contrast of the ultrasound image. Then, the image quality adjustment unit 20 narrows a dynamic range, and thereby can adjust the image quality of the ultrasound image U. Here, as shown by a solid line in FIG. 6, in a case where the brightness gradient at the boundary portion between the bladder region R1 and the differential region R3 is very large and larger than the fifth threshold value, determination is made that the shape of the bladder region R1 depends on not the image quality but the shape of the bladder itself.

Further, as shown in FIG. 5, in a case where the bladder region R1 has the concave portion A in the central part of the shallow portion, the bladder extraction success/failure determination unit 19 determines that the bladder region R1 does not represent the bladder having the reference pattern consisting of the normal bladder pattern, but the shape of the bladder region R1 on which the bladder extraction success/failure determination unit 19 makes such determination is not limited to the shape shown in FIG. 5.

Figure 7:
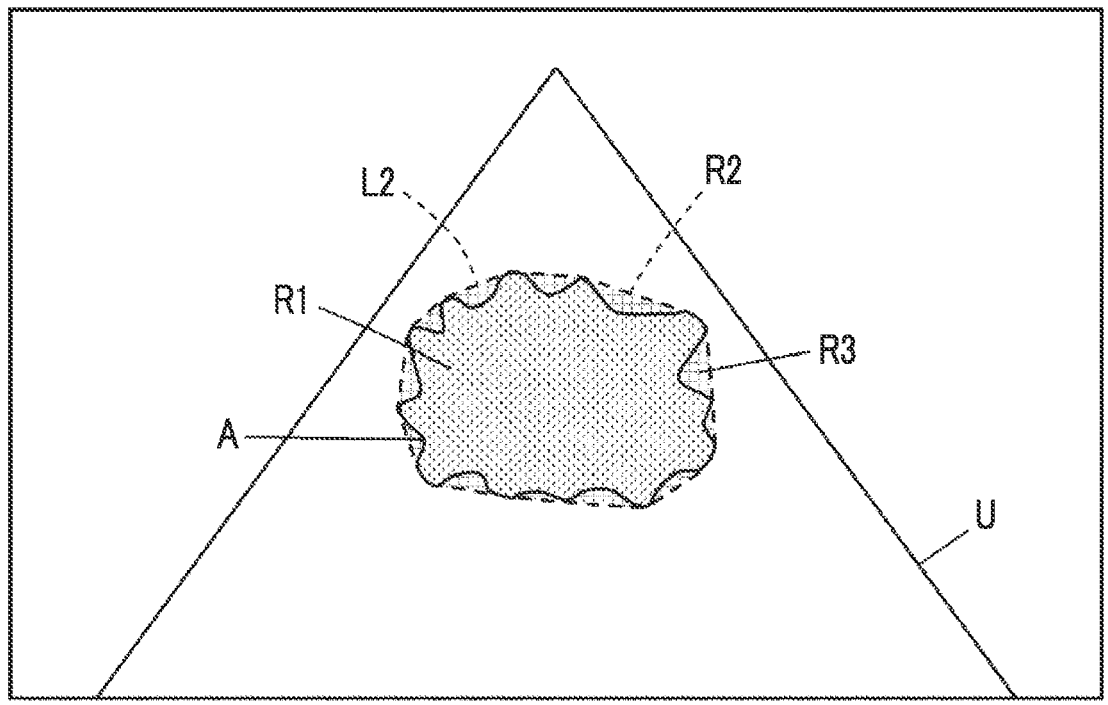
FIG. 7 is a diagram schematically showing another example of the bladder region.

As shown in FIG. 7, for example, in a case where the bladder region R1 extracted by the bladder extraction unit 18 has the plurality of concave portions A along the circumference of the bladder region R1, and a ratio of the length along the circumference to the area of the bladder region R1 exceeds a predetermined threshold value due to presence of the differential region R3 between the convex hull region R2 of the bladder region R1 and the bladder region R1, the bladder extraction success/failure determination unit 19 may determine that the bladder region R1 does not represent the bladder having the reference pattern. Here, in a case where an envelope L2 having a polygonal shape, which envelopes the bladder region R1, is defined, the convex hull region R2 refers to a region surrounded by the envelope L2 and including the bladder region R1. The differential region R3 is a region obtained by subtracting the bladder region R1 from the convex hull region R2.

Also, in a case where the bladder region R1 has the shape shown in FIG. 7, the image quality adjustment unit 20 may adjust the image quality of the ultrasound image U based on the brightness of the bladder region R1 and the brightness of differential region R3 in the same manner as in the case where the bladder region R1 has the shape shown in FIG. 5.

Figure 8:
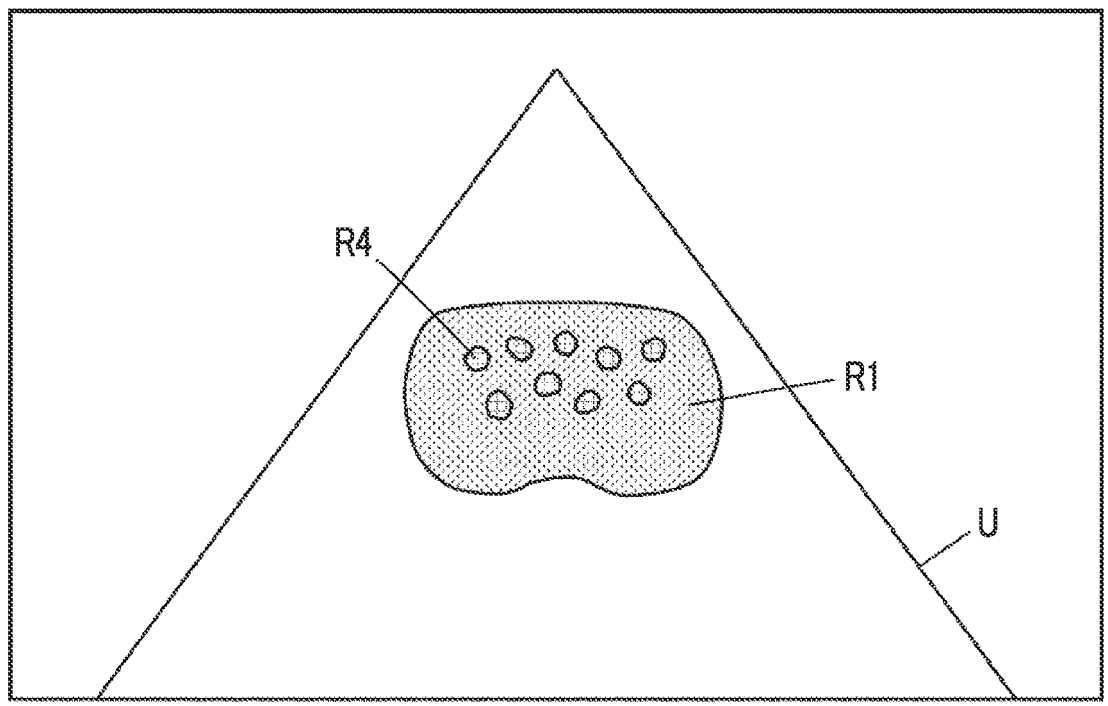
FIG. 8 is a diagram schematically showing still another example of the bladder region.

Further, as shown in FIG. 8, for example, in a case where the bladder region R1 has void portions R4 inside thereof, and a ratio of a sum of areas of the void portions R4 to an area of the bladder region R1 exceeds a predetermined threshold value, the bladder extraction success/failure determination unit 19 may determine that the bladder region R1 does not represent the bladder having the reference pattern. The void portion R4 refers to a portion existing isolated inside the bladder region R1 and having the brightness different from the brightness of the bladder region R1.

In this case, the image quality adjustment unit 20 determines that the bladder region R1 is too brightly depicted due to the high gain of the ultrasound image U. Then, the image quality adjustment unit 20 lowers the gain, and thereby can adjust the image quality of the ultrasound image U.

Further, the kind of the image quality adjustment performed on one ultrasound image U by the image quality adjustment unit 20 is not limited to one, and may be two or more. For example, in a case where the bladder region R1 has the shape shown in FIG. 5, the image quality adjustment unit 20 lowers the gain of the ultrasound image and narrows the dynamic range, based on the brightness of the bladder region R1 and the brightness of the differential region R3. As a result, the bladder region R1 can be depicted more clearly, and the accuracy with which the ultrasound diagnostic apparatus 1 extracts the bladder can be improved.

The kind of the abnormal bladder pattern stored in the bladder pattern storage unit 22 is not limited to one, and for example, the plurality kinds of abnormal bladder patterns, such as a shape of a bladder with an enlarged prostate, a shape of a bladder with an enlarged cervix, a shape of a bladder with an indwelling balloon, or a shape of a bladder of a subject suffering from cystitis may be stored in the bladder pattern storage unit 22.

In this case, for example, while the reference pattern setting unit 21 sequentially switches the plurality of abnormal bladder patterns stored in the bladder pattern storage unit 22 as the reference pattern, the bladder extraction success/failure determination unit 19 may repeatedly determine whether or not the bladder region R1 represents the bladder having the reference pattern. As a result, the accuracy of extracting the bladder can be improved.

In addition, in a case where the bladder pattern storage unit 22 stores the plurality of the abnormal bladder patterns, the reference pattern setting unit may include a pattern classifier (not shown) that classifies which of the plurality of abnormal bladder patterns stored in the bladder pattern storage unit the bladder region R1 extracted by the bladder extraction unit 18 corresponds to. With the pattern classifier, the abnormal bladder patterns corresponding to the bladder region R1 are automatically classified and selected and as a result, the number of determination by the bladder extraction success/failure determination unit 19 can be reduced and the bladder can be extracted more quickly.

EXPLANATION OF REFERENCES

1: ultrasound diagnostic apparatus
2: ultrasound probe
3: diagnostic apparatus body
11: transducer array
12: transmission unit
13: reception unit
14: image generation unit
15: display controller
16: display unit
17: image acquisition unit
18: bladder extraction unit
19: bladder extraction success/failure determination unit
20: image quality adjustment unit
21: reference pattern setting unit
22: bladder pattern storage unit
23: apparatus controller
24: input unit
25: storage unit
26: processor
27: amplification unit
28: AD conversion unit
29: beamformer
30: signal processing unit
31: DSC
32: image processing unit
33: guide unit
L1: straight line
L2: envelope
R1: bladder region
R2: convex hull region
R3: differential region
R4: void portion
U: ultrasound image

What is claimed is:

1. An ultrasound diagnostic apparatus comprising:
an ultrasound probe;
a display that displays an ultrasound image of a subject; and
a processor configured to function as
an image acquisition unit that acquires the ultrasound image of the subject by performing transmission and reception of an ultrasound beam to and from the ultrasound probe,
a bladder pattern storage unit that stores a normal bladder pattern and an abnormal bladder pattern,
a reference pattern setting unit that sets one of the normal bladder pattern and the abnormal bladder pattern stored in the bladder pattern storage unit, as a reference pattern,
a bladder extraction unit that extracts a bladder region from the ultrasound image acquired by the image acquisition unit,
a bladder extraction success/failure determination unit that determines whether or not the bladder region extracted by the bladder extraction unit represents a bladder having the reference pattern set by the reference pattern setting unit; and
an image quality adjustment unit that adjusts an image quality of the ultrasound image,
wherein in a case where the reference pattern setting unit sets the normal bladder pattern as the reference pattern and the bladder extraction success/failure determination unit determines that the bladder region does not represent a bladder having the reference pattern, the image quality adjustment unit adjusts the image quality of the ultrasound image and the bladder extraction success/failure determination unit determines whether or not the bladder region represents the bladder having the reference pattern for the ultrasound image of which the image quality is adjusted, and
in a case where the bladder extraction success/failure determination unit determines that the bladder region does not represent the bladder having the reference pattern even in the ultrasound image of which the image quality is adjusted by the image quality adjustment unit, the reference pattern setting unit sets the abnormal bladder pattern as the reference pattern and the bladder extraction success/failure determination unit determines whether or not the bladder region represents a bladder having the reference pattern consisting of the abnormal bladder pattern.

2. The ultrasound diagnostic apparatus according to claim 1,
wherein in a case where the bladder region extracted by the bladder extraction unit has a plurality of concave portions along a circumference of the bladder region and a ratio of a length along the circumference to an area of the bladder region exceeds a predetermined threshold value due to presence of a differential region between a convex hull region of the bladder region and the bladder region, the bladder extraction success/failure determination unit determines that the bladder region does not represent the bladder having the reference pattern.

3. The ultrasound diagnostic apparatus according to claim 1,
wherein in a case where the bladder region extracted by the bladder extraction unit has a concave portion in a central part of a shallow portion and a ratio of an area of a differential region between a convex hull region of the bladder region and the bladder region to an area of the bladder region exceeds a predetermined threshold value, the bladder extraction success/failure determination unit determines that the bladder region does not represent the bladder having the reference pattern.

4. The ultrasound diagnostic apparatus according to claim 2,
wherein in a case where a median value of brightness in the bladder region exceeds a predetermined first threshold value and a variance value of brightness in the differential region is equal to or less than a predetermined second threshold value, the image quality adjustment unit lowers a gain to adjust the image quality of the ultrasound image.

5. The ultrasound diagnostic apparatus according to claim 3,
wherein in a case where a median value of brightness in the bladder region exceeds a predetermined first threshold value and a variance value of brightness in the differential region is equal to or less than a predetermined second threshold value, the image quality adjustment unit lowers a gain to adjust the image quality of the ultrasound image.

6. The ultrasound diagnostic apparatus according to claim 2, wherein in a case where a difference between a median value of brightness in the bladder region and a median value of brightness in the differential region is equal to or less than a predetermined third threshold value and a variance value of brightness in the differential region exceeds a predetermined fourth threshold value, the image quality adjustment unit narrows a dynamic range to adjust the image quality of the ultrasound image.

7. The ultrasound diagnostic apparatus according to claim 3,
wherein in a case where a difference between a median value of brightness in the bladder region and a median value of brightness in the differential region is equal to or less than a predetermined third threshold value and a variance value of brightness in the differential region exceeds a predetermined fourth threshold value, the image quality adjustment unit narrows a dynamic range to adjust the image quality of the ultrasound image.

8. The ultrasound diagnostic apparatus according to claim 2,
wherein in a case where a brightness gradient from the bladder region to the differential region is equal to or less than a predetermined fifth threshold value, the image quality adjustment unit narrows a dynamic range to adjust the image quality of the ultrasound image.

9. The ultrasound diagnostic apparatus according to claim 3,
wherein in a case where a brightness gradient from the bladder region to the differential region is equal to or less than a predetermined fifth threshold value, the image quality adjustment unit narrows a dynamic range to adjust the image quality of the ultrasound image.

10. The ultrasound diagnostic apparatus according to claim 1,
wherein in a case where a ratio of an area of a void portion formed inside the bladder region to an area of the bladder region extracted by the bladder extraction unit exceeds a predetermined threshold value, the bladder extraction success/failure determination unit determines that the bladder region does not represent the bladder having the reference pattern.

11. The ultrasound diagnostic apparatus according to claim 10,
wherein the image quality adjustment unit lowers a gain to adjust the image quality of the ultrasound image.

12. The ultrasound diagnostic apparatus according to claim 1,
wherein the bladder pattern storage unit stores at least one of a shape of a bladder with an enlarged prostate or cervix, a shape of a bladder with an indwelling balloon, or a shape of a bladder suffering from cystitis, as the abnormal bladder pattern.

13. The ultrasound diagnostic apparatus according to claim 12,
wherein the bladder pattern storage unit stores a plurality of the abnormal bladder patterns, and
the reference pattern setting unit includes a pattern classifier that classifies which of the plurality of abnormal bladder patterns stored in the bladder pattern storage unit the bladder region extracted by the bladder extraction unit corresponds to.

14. The ultrasound diagnostic apparatus according to claim 1
wherein the processor is further configured to function as
a guide unit that provides guidance on newly acquiring an ultrasound image by the image acquisition unit, in a case where the bladder extraction success/failure determination unit determines that the bladder region does not represent the bladder having the reference pattern even in a state in which the reference pattern setting unit sets the abnormal bladder pattern as the reference pattern.

15. A control method of an ultrasound diagnostic apparatus, comprising:
acquiring an ultrasound image of a subject by performing transmission and reception of an ultrasound beam to and from an ultrasound probe;
displaying the acquired ultrasound image;
storing a normal bladder pattern and an abnormal bladder pattern;
setting one of the normal bladder pattern and the abnormal bladder pattern, as a reference pattern;
extracting a bladder region from the acquired ultrasound image;
determining whether or not the extracted bladder region represents a bladder having the set reference pattern;
adjusting an image quality of the ultrasound image in a case where determination is made that the bladder region does not represent a bladder having the reference pattern in a state in which the normal bladder pattern is set as the reference pattern;
determining whether or not the bladder region represents the bladder having the reference pattern for the ultrasound image of which the image quality is adjusted; and
setting the abnormal bladder pattern as the reference pattern in a case where determination is made that the bladder region does not represent the bladder having the reference pattern even in the ultrasound image of which the image quality is adjusted, and determining whether or not the bladder region represents a bladder having the reference pattern consisting of the abnormal bladder pattern.

* * * * *